United States Patent [19]
Kataoka et al.

[11] Patent Number: 5,929,177
[45] Date of Patent: Jul. 27, 1999

[54] BLOCK POLYMER HAVING FUNCTIONAL GROUPS AT BOTH ENDS

[75] Inventors: Kazunori Kataoka, 1083-4, Ohmuro, Kashiwa-shi, Chiba 277; Masao Kato; Yukio Nagasaki, both of Ibaraki; Teruo Okano, Chiba, all of Japan

[73] Assignee: Kazunori Kataoka, Kashiwa, Japan

[21] Appl. No.: 09/011,329

[22] PCT Filed: Aug. 5, 1996

[86] PCT No.: PCT/JP96/02200

§ 371 Date: Feb. 5, 1998

§ 102(e) Date: Feb. 5, 1998

[87] PCT Pub. No.: WO97/06202

PCT Pub. Date: Feb. 20, 1997

[30] Foreign Application Priority Data

Aug. 10, 1995 [JP] Japan ................... 7-204547

[51] Int. Cl.$^6$ ............... C08L 71/02; C08G 65/32; A61K 31/765
[52] U.S. Cl. ............... 525/408; 525/258; 424/78.17; 424/78.31; 424/78.37; 424/501; 528/409
[58] Field of Search ............... 525/408, 258; 424/78.17, 78.31, 78.37, 501; 528/409

[56] References Cited

U.S. PATENT DOCUMENTS

| | | | |
|---|---|---|---|
| 5,008,109 | 4/1991 | Tin | 428/402.2 |
| 5,410,016 | 4/1995 | Hubbell et al. | 525/413 |
| 5,449,513 | 9/1995 | Yokoyama et al. | 424/78.17 |
| 5,548,035 | 8/1996 | Kim et al. | 525/408 |

FOREIGN PATENT DOCUMENTS

| | | |
|---|---|---|
| 60-258109 | 12/1985 | Japan . |
| 2-224822 | 9/1990 | Japan . |
| 3-287545 | 12/1991 | Japan . |
| 4-99731 | 3/1992 | Japan . |
| 5-117385 | 4/1993 | Japan . |
| 7-216095 | 8/1995 | Japan . |
| 7-247355 | 9/1995 | Japan . |
| 8-100026 | 4/1996 | Japan . |
| 8-226082 | 9/1996 | Japan . |

*Primary Examiner*—James J. Seidleck
*Assistant Examiner*—Olga Asinovsky
*Attorney, Agent, or Firm*—Scully, Scott, Murphy & Presser

[57] ABSTRACT

The present invention provides a block polymer which has functional groups on its both ends, and which comprises hydrophilic/hydrophobic segments. As for the functional groups on its both ends, the block polymer has amino group, carboxyl group or mercapto group on α-terminal, and hydroxyl group, carboxyl group, aldehyde group or vinyl group on ω-terminal. Hydrophilic segment comprises polyethylene oxide, while hydrophobic segment is derived from lactide, lactone or (meth)acrylic acid ester. The block polymer of this invention forms a polymeric micelle which is usable as bio-compatible materials.

10 Claims, No Drawings

BLOCK POLYMER HAVING FUNCTIONAL GROUPS AT BOTH ENDS

TECHNICAL FIELD

The present invention relates to a block polymer which has functional groups on its both ends, a method for the production thereof and its application to polymeric micelle. More detailedly, this invention discloses a polymer which has functional groups on its both ends while having, in its main chain, a polyethylene oxide chain as a hydrophilic segment and another chain derived from polyester or (meth) acrylic acid derivative as a hydrophobic segment.

In this invention, the term "polymer" includes oligomer.

BACKGROUND ART

A polymeric micelle or nanosphere composed of a hydrophilic/hydrophobic type block polymer wherein a hydrophilic polymer like polyethylene oxide is combined with a hydrophobic polymer at the molecular level is now attracting attention as a carrier for drug delivery or the like. Said polymeric micelle and nanosphere have been prepared from a hydrophilic/hydrophobic type block polymer wherein a hydrophilic polymer is combined with a hydrophobic polymer at the molecular level.

In conventional processes to produce a hydrophilic/hydrophobic type block polymer, however, there is a limitation on the species of terminal functional groups to be introduced, and there have only been proposed block polymers whose functional groups are restricted to methoxy or hydroxyl group. If optional functional groups were successfully introduced onto the micelle surface at an optional proportion, it would become possible to provide a functional polymeric micelle which could be useful for drug delivery to certain organs.

Thus, the object of this invention is to provide a block polymer, which has functional groups on both ends of its main chain, as a polyfunctional polymer which is capable of forming a polymeric micelle.

Disclosure of Invention

The inventors of this invention have found out that there can easily be produced a block polymer which has a protected or non-protected amino group, carboxyl group or mercapto group on one end of molecule and various functional groups on the other end, when an alkylene, phenylene or phenylalkylene derivative having a certain kind of protected amino group, carboxyl group or mercapto group and a hydroxyl group is utilized as a living polymerization initiator and when ethylene oxide and lactide or lactone or (meth)acrylic acid ester are polymerized as monomers, and further when electrophilic agent is made to react if necessary.

They have also confirmed that a block polymer obtained in this manner forms a polymeric micelle which is quite stable in an aqueous solvent.

This invention thus provides a block polymer which has functional groups on both ends of molecule and which is represented by formula (I) below:

  (I)

wherein X denotes an alkyl group having 1 to 10 carbon atoms which has one or two substituents selected from the group consisting of amino group blocked with amino-protecting group, carboxyl group blocked with carboxyl-protecting group and mercapto group blocked with mercapto-protecting group, or phenyl or phenyl-alkyl group which has the above-mentioned substituents on benzene ring;

Y denotes a group selected from the group consisting of the following recurring units

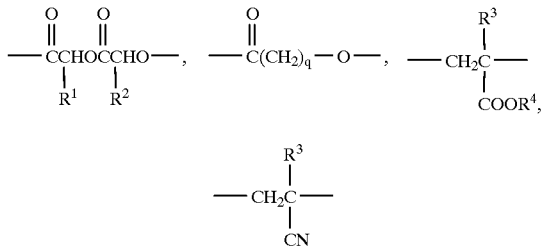

wherein $R^1$ and $R^2$ independently denote hydrogen atom or alkyl group having 1 to 5 carbon atoms; $R^3$ denotes hydrogen atom or methyl group; $R^4$ denotes alkyl group having 1 to 5 carbon atoms which is substituted with hydroxyl group under circumstances; q denotes an integer of 2–5;

Z denotes functional group selected from the group consisting of hydrogen atom, acryloyl group ($CH_2$=CH—CO—), methacryloyl group ($CH_2$=C($CH_3$)—CO—), vinylbenzyl group

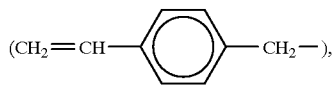

allyl group ($CH_2$=CH—$CH_2$—), p-toluenesulfonyl group

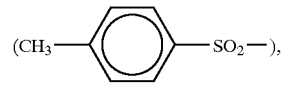

mercapto group, alkyl group having amino group which is mono- or di-substituted under circumstances with alkyl group having 1 to 5 carbon atoms, alkyl group having carboxyl group or its ester group, alkyl group having acetal group, and halogen atom; and m and n independently denote an integer of 2–10,000.

The above block polymer can be easily produced from the living polymer represented by the following formula (II) in accordance with the present invention. This invention therefore provides not only a process to produce the block polymer of formula (I) with use of the living polymer represented by the following formula (II) as a starting material, but also the living polymer of formula (II) per se which is usable for the further production of a block polymer having hydrophilic or hydrophobic segment.

  (II)

wherein Xa denotes an alkyl group having 1 to 10 carbon atoms which has one or two substituents selected from the group consisting of amino group blocked with amino-protecting group, carboxyl group blocked with carboxyl-protecting group and mercapto group blocked with mercapto-protecting group, or denotes phenyl or phenyl-alkyl group which has the above-mentioned substituents on benzene ring;

Y and Ya denote a group selected from the group consisting of the groups represented by the following formulae

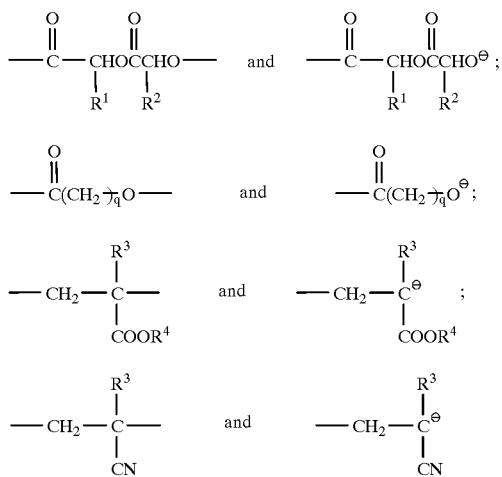

wherein $R^1$ and $R^2$ independently denote hydrogen atom or alkyl group having 1 to 5 carbon atoms; $R^3$ denotes hydrogen atom or methyl group; $R^4$ denotes alkyl group having 1 to 5 carbon atoms which is substituted with hydroxyl group under circumstances; and q denotes an integer of 2–5;

$M^\oplus$ denotes cation of alkaline metal selected from the group consisting of lithium, sodium, potassium and cesium; and m and n independently denote an integer of 2–10,000.

The block polymer of the above formula (I) forms, when treated in a solvent, a stable polymeric micelle which contains said block polymer as an active ingredient. Thus, this invention provides also such a polymeric micelle.

As will be seen from their constituent components, the block polymers of formula (I) and polymeric micelles prepared therefrom are expected to have high bio-affinity or bioavailability. These block polymers or polymeric micelles as they are, or polymers which are further prepared therefrom with use of one or both of their terminal functional groups can therefore be used for the production of materials which are directly applicable to living organism such as carrier for drug delivery. Moreover, since this invention provides a polymeric micelle which is quite stable in an aqueous solvent, the polymer of this invention is therefore useful also for drug delivery to a certain organ.

DETAILED DESCRIPTION OF INVENTION

The block polymer of formula (I), whose group X is substituted with amino group, carboxyl group or mercapto group which may be protected, carries a free functional group at one terminal of polymer when protected as it is or when deprotected. In this specification, said terminal is called α-terminal for convenience sake.

The above-mentioned protecting groups include amino-protecting group, carboxy-protecting group and mercapto-protecting group which are usually used in this field. Any of these groups can be employed so long as they can be eliminated by means of hydrolysis or catalytic hydrogenation and have no adverse effects on the living polymerization of this invention.

Concrete examples of amino-protecting group include benzylidene group which forms Schiff base (imino group) together with nitrogen atom of amino group and whose benzene ring may be substituted with alkyl group having 1 to 3 carbon atoms, in particular methyl group, or halogen atom, in particular fluorine or chlorine, preferably non-substituted benzylidene group; alkoxycarbonyl having 1 to 5 carbon atoms, in particular tert-butoxycarbonyl group; and silyl group having three groups selected from the group consisting of alkyl group having 1 to 3 carbon atoms and phenyl group, in particular trimethylsilyl, triethylsilyl and dimethyl-phenyl silyl. Amino group blocked with amino-protecting group includes cyano group which forms amino group when reduced by a certain way.

Concrete examples of carboxy-protecting group include alkoxy group having 1 to 5 carbon atoms which constitutes a part of ester with carboxyl group, in particular methoxy, ethoxy, n-propoxy, iso-propoxy, n-butoxy, tert-butoxy, phenyl-substituted methoxy, in particular benzyl oxy, diphenyl methoxy and triphenyl methoxy. Carboxyl group blocked with carboxy-protecting group includes cyano group which forms carboxyl group when hydrolyzed in a certain way.

Concrete examples of mercapto-protecting group include phenyl, benzyl, trimethylsilyl, acetyl, o-, m-, p-methyl benzyl, triethyl silyl, o-, m-, p-tolyl and tert-butyldimethyl silyl.

Examples of alkyl group which constitutes group X include such alkyl groups as are capable of forming straight chain- or branched-alkylene group, concretely methyl, ethyl, n-propyl, iso-propyl, n-butyl, sec-butyl, n-pentyl, sec-pentyl, n-hexyl, heptyl and decyl group, in particular, methyl, ethyl, n-propyl and n-butyl.

Group X may be composed of phenyl or phenyl-alkyl, in particular benzyl or phenethyl.

Such being the case, concrete examples of group X (a part of Xa) which has an amino-protecting group include, not restrictively, 1- or 2-benzalimino ethyl group, 1-, 2- or 3-benzalimino propyl group, 1-, 2-, 3- or 4-benzalimino butyl group, 1-, 2-, 3-, 4- or 5-benzalimino pentyl group, 2-, 3- or 4-benzalimino phenyl group, 2-, 3- or 4-benzalimino benzyl group, 2-, 3- or 4-benzalimino phenethyl group, N. N-(bistrimethyl silyl) aminomethyl group, 1- or 2-N, N-(bistrimethyl silyl) aminoethyl group, 1-, 2- or 3-N, N-(bistrimethyl silyl) aminopropyl group, 1-, 2-, 3- or 4-N, N-(bistrimethyl silyl) aminobutyl group, 1-, 2-, 3-, 4- or 5-N, N-(bistrimethyl silyl) aminopentyl group, 2-, 3- or 4-N, N-(bistrimethyl silyl) aminophenyl group, 2-, 3- or 4-N, N-(bistrimethyl silyl) aminobenzyl group, 2-, 3- or 4-N, N-(bistrimethyl silyl) aminophenethyl group, N-trimethyl silyl-N-methylaminomethyl group, 1- or 2-N-trimethyl silyl-N-methylaminoethyl group, 1-, 2- or 3-N-trimethyl silyl-N-methyl aminopropyl group, 1-, 2-, 3- or 4-N-trimethyl silyl-N-methyl aminobutyl group, 1-, 2-, 3-, 4- or 5-N-trimethyl silyl-N-methylaminopentyl group, 2-, 3- or 4-N-trimethyl silyl-N-methylaminophenyl group, 2-, 3- or 4-N-trimethyl silyl-N-methylaminobenzyl group, 2-, 3- or 4-N-trimethyl silyl-N-methylaminophenethyl group, N-trimethyl silyl-N-ethylaminomethyl group, 1- or 2-N-trimethyl silyl-N-ethylaminoethyl group, 1-, 2- or 3-N-trimethyl silyl-N-ethylaminopropyl group, 1-, 2-, 3- or 4-N -trimethyl silyl-N -ethyl aminobutyl group, 1-, 2 -, 3-, 4- or 5-N-trimethyl silyl-N-ethylaminopentyl group, 2-, 3- or 4-N-trimethyl silyl-N-ethylaminophenyl group, 2-, 3- or 4-N-trimethyl silyl-N-ethylaminobenzyl group, 2-, 3- or 4-N-trimethyl silyl-N-ethylaminophenethyl group, dimethylaminomethyl group, 1- or 2-dimethylaminoethyl group, 1-, 2- or 3-dimethylaminopropyl group, 1-, 2-, 3- or 4-dimethylaminobutyl group, 1-, 2-, 3-, 4- or 5-dimethylaminopentyl group, 2-, 3- or 4-dimethylaminophenyl group, 2-, 3- or 4-dimethylaminobenzyl group, 2-, 3- or 4-dimethylaminophenethyl group, diethylaminomethyl group, 1- or 2-diethylaminoethyl group, 1-, 2- or 3-diethylaminopropyl group, 1-, 2-, 3- or 4-diethylaminobutyl group, 1-, 2-, 3-, 4- or 5-diethylaminopentyl group, 2-, 3- or 4-diethylaminophenyl group, 2-, 3- or 4-diethylaminobenzyl group, 2-, 3- or 4-diethylaminophenethyl group. Incidentally, when the protecting group is other than benzylidene, the protected amino group can be methyl amino, ethyl amino or propyl amino, or cyano group.

Concrete examples of group X (a part of Xa) which has a carboxy-protecting group include, not restrictively, methoxycarbonyl methyl group, 1- or 2-methoxycarbonyl ethyl group, 1-, 2- or 3-methoxycarbonyl propyl group, 1-, 2-, 3- or 4-methoxycarbonyl butyl group, 1-, 2-, 3-, 4- or 5-methoxycarbonyl pentyl group, 2-, 3- or 4-methoxycarbonyl phenyl group, 2-, 3- or 4-methoxycarbonyl benzyl group, 2-, 3- or 4-methoxycarbonyl phenethyl group, ethoxycarbonyl methyl group, 1- or 2-ethoxycarbonyl ethyl group, 1-, 2- or 3-ethoxycarbonyl propyl group, 1-, 2-, 3- or 4-ethoxycarbonyl butyl group, 1-, 2-, 3-, 4- or 5-ethoxycarbonyl benzyl group, 2-, 3- or 4-ethoxycarbonyl phenyl group, 2-, 3- or 4-ethoxycarbonyl benzyl group, 2-, 3- or 4-ethoxycarbonyl phenethyl group, tert-butoxycarbonyl methyl group, 1- or 2-tert-butoxycarbonyl ethyl group, 1-, 2- or 3-tert-butoxycarbonylpropyl group, 1-, 2-, 3- or 4-tert-butoxycarbonylbutyl group, 1-, 2-, 3-, 4- or 5-tert-butoxycarbonylpentyl group, 2-, 3- or 4-tert-butoxycarbonylphenyl group, 2-, 3- or 4-tert-butoxycarbonylbenzyl group, 2-, 3- or 4-tert-butoxycarbonylphenethyl group, nitrile group such as 3-cyanopropyl group.

Concrete examples of group X (a part of Xa) which has a mercapto-protecting group include, not restrictively, phenylmercapto methyl group, 1- or 2-phenylmercapto ethyl group, 1-, 2- or 3-phenylmercapto propyl group, 1-, 2-, 3- or 4-phenylmercapto butyl group, 1-, 2-, 3-, 4- or 5-phenylmercapto pentyl group, 2-, 3- or 4-phenylmercapto phenyl group, 2-, 3- or 4-phenylmercapto benzyl group, 2-, 3- or 4-phenylmercapto phenethyl group, benzylmercaptomethyl group, 1- or 2-benzylmercapto ethyl group, 1-, 2- or 3-benzylmercapto-propyl group, 1-, 2-, 3- or 4-benzylmercapto butyl group, 1-, 2-, 3-, 4- or 5-benzylmercapto pentyl group, 2-, 3- or 4-benzylmercapto phenyl group, 2-, 3- or 4-benzylmercapto benzyl group, 2-, 3- or 4-benzylmercapto phenethyl group, tolyl-mercapto methyl group, 1- or 2-tolylmercapto ethyl group, 1-, 2- or 3-tolylmercapto propyl group, 1-, 2-, 3- or 4-tolyl-mercapto butyl group, 1-, 2-, 3-, 4- or 5-tolylmercapto pentyl group, 2-, 3- or 4-tolylmercapto phenyl group, 2-, 3- or 4-tolylmercapto benzyl group, 2-, 3- or 4-tolylmercapto phenethyl group, and acetyl thioethyl group.

Another segment Y in addition to the oxyethylene segment in formula (I) is a group which is derived from a cyclic diester formed by subjecting two molecules of α-hydroxy acid to dehydration and which is represented by the following formula:

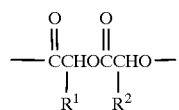

wherein $R^1$ and $R^2$ independently denote hydrogen atom or alkyl group having 1 to 5 carbon atoms.

The above-mentioned cyclic diester may be formed from either similar or different α-hydroxy acids, but is preferably derived from two molecules of similar α-hydroxy acids. In particularly preferable example of Y, both $R^1$ and $R^2$ denote either hydrogen atom or methyl group.

Y can also be a group derived from such a lactone as is represented by the following formula, concretely α-lactone, β-lactone, γ-lactone, δ-lactone or ε-lactone:

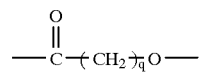

wherein q denotes an integer of 2–5.

The mark q preferably denotes integer 4 (Y is derived from γ-lactone) or 5 (Y is derived from δ-lactone).

Y can further be a group derived from (meth)acrylic acid ester or (meth)acrylonitrile which is represented by the following formula:

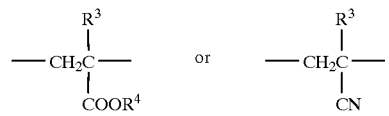

wherein $R^3$ denotes hydrogen atom or methyl group, and $R^4$ denotes an alkyl group having 1 to 5 carbon atoms which is substituted with hydroxyl group which may be protected under circumstances.

Concrete examples of $R^4$ include methyl, ethyl, n-propyl, n-butyl, tert-butyl, 2-trimethylsiloxy ethyl, 2-(tert-butyldimethylsiloxy ethyl) and 2-hydroxyethyl. In this specification, the terms (meth)acrylic acid and (meth)acrylonitrile each comprehend methacrylic acid and acrylic acid, and methacrylonitrile and acrylonitrile.

As for the number of oxyethylene segment in formula (I), m can be any integer of 2–10,000. In accordance with the production process of this invention, almost mono-dispersible (mono-modal) segment having desired number of m can be obtained by means of adjusting the proportion of the amount of ethylene oxide to the initiator $X-O^{\ominus}M^{\oplus}$ for the living anion polymerization. The block polymer of this invention is therefore conveniently used for the production of materials applicable to living organism, and the above number m can be appropriately determined according to concrete use of the polymer.

As for segment Y, similarly, any desirable number of n can be selected from integer 2–10,000 so that molecular weight distribution may be quite narrow.

The mark Z denotes a functional group on the other terminal (hereinafter called ω-terminal for convenience sake; the terminal on the right side in the structure of formula (I)) besides the α-terminal of the above block polymer.

Although any functional group can be introduced for Z by means of electrophilic substitution reaction onto the anion portion of ω-terminal of the living block polymer of formula (II), such a group as to improve bio-compatibility or as is usable for further reactions is preferably employed in view of the objective of this invention.

Such being the case, examples of group Z in formula (I) include hydrogen atom (which forms hydroxyl group when Y is in particular derived from lactide or lactone), acryloyl group ($CH_2$=CH—CO—), methacryloyl group ($CH_2$=C($CH_3$)—CO—), vinylbenzyl group

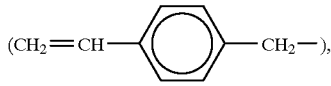

allyl group ($CH_2$=CH—$CH_2$—), alkyl group having carboxyl group or its ester group such as ethyloxy carbonylmethyl group ($C_2H_5OCOCH_2$—), methyloxy carbonylmethyl group ($CH_3OCOCH_2$—), carboxymethyl group (HOOC—$CH_2$—), ethyloxy carbonylethyl group ($C_2H_5OCOC_2H_4$—), carboxyethyl group (HOOC—$CH_2CH_2$—); alkyl group having aldehyde or its acetal group such as formylethane (OCH—$CH_2CH_2$—), 3.3-dimethoxypropane (($CH_3O)_2CHCH_2CH_2$—); p-toluenesulfonyl group

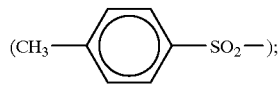

mercapto group; halogen atom such as chlorine, bromine and iodine; alkyl group which is mono- or di-substituted under circumstances with alkyl group having 1 to 5 carbon atoms such as 2-aminoethyl, N-methyl-2-amino-ethyl, N,N-dimethyl-2-aminoethyl. Incidentally, mercapto group and the followings can be employed only when segment Y is derived from lactide or lactone. When segment Y is derived from (meth)acrylic acid ester or (meth)acrylonitrile, ethylene oxide for example is added to the ω-terminal of the living block polymer of formula (II) so that 2-hydroxyethyl group may be formed, and, thereafter, through its hydroxyl group, there can be introduced the above-mentioned mercapto group, halogen atom and alkyl group which is mono- or di-substituted under circumstances with alkyl group having 1 to 5 carbon atoms.

Table below shows examples of typical block polymer of this invention which the above groups (or segments) are combined with one another to constitute.

TABLE $$X-O-(CH_2CH_2O)_m-(Y)_n-Z \quad (I)$$

wherein m and n are each optional integer of 2–10,000.

| Compound NO. | X | Y | Z |
|---|---|---|---|
| 1 | ⟨phenyl⟩-CH=N-$CH_2CH_2$— | —CCHOCCHO— with O, O double bonds and $CH_3$, $CH_3$ | H |
| 2 | $H_2N$—$CH_2CH_2$— | —CCHOCCHO— with O, O double bonds and $CH_3$, $CH_3$ | H |
| 3 | ⟨phenyl⟩-CH=N-$CH_2CH_2$— | —CCHOCCHO— with O, O double bonds and $CH_3$, $CH_3$ | CC=$CH_2$ with O double bond and $CH_3$ |
| 4 | $H_2N$—$CH_2CH_2$— | —CCHOCCHO— with O, O double bonds and $CH_3$, $CH_3$ | CC=$CH_2$ with O double bond and $CH_3$ |
| 5 | NC—($CH_2)_3$— | —CCHOCCHO— with O, O double bonds and $CH_3$, $CH_3$ | H |
| 6 | NC—($CH_2)_3$— | —CCHOCCHO— with O, O double bonds and $CH_3$, $CH_3$ | CC=$CH_2$ with O double bond and $CH_3$ |

TABLE-continued $$X-O-(CH_2CH_2O)_m-(Y)_n-Z \quad (I)$$

wherein m and n are each optional integer of 2–10,000.

| Compound NO. | X | Y | Z |
|---|---|---|---|
| 7 | $NC-(CH_2)_3-$ | $-\underset{CH_3}{\underset{|}{C}}(=O)CH-O-\underset{CH_3}{\underset{|}{C}}(=O)CH-O-$ | $-C(=O)CH=CH_2$ |
| 8 | $NC-(CH_2)_3-$ | $-C(=O)(CH_2)_5O-$ | H |
| 9 | $NC-(CH_2)_3-$ | $-C(=O)(CH_2)_5O-$ | $-C(=O)C(CH_3)=CH_2$ |
| 10 | $NC-(CH_2)_3-$ | $-C(=O)(CH_2)_5O-$ | $-C(=O)CH=CH_2$ |
| 11 | $H_2N-(CH_2)_4-$ | $-\underset{CH_3}{\underset{|}{C}}(=O)CH-O-\underset{CH_3}{\underset{|}{C}}(=O)CH-O-$ | H |
| 12 | $H_2N-(CH_2)_4-$ | $-\underset{CH_3}{\underset{|}{C}}(=O)CH-O-\underset{CH_3}{\underset{|}{C}}(=O)CH-O-$ | $-C(=O)C(CH_3)=CH_2$ |
| 13 | $H_2N-(CH_2)_4-$ | $-\underset{CH_3}{\underset{|}{C}}(=O)CH-O-\underset{CH_3}{\underset{|}{C}}(=O)CH-O-$ | $-C(=O)CH=CH_2$ |
| 14 | $H_2N-(CH_2)_4-$ | $-C(=O)(CH_2)_5O-$ | H |
| 15 | $H_2N-(CH_2)_4-$ | $-C(=O)(CH_2)_5O-$ | $-C(=O)C(CH_3)=CH_2$ |
| 16 | $H_2N-(CH_2)_4-$ | $-C(=O)(CH_2)_5O-$ | $-C(=O)CH=CH_2$ |
| 17 | $NC-(CH_2)_3-$ | $-\underset{CH_3}{\underset{|}{C}}(=O)CH-O-\underset{CH_3}{\underset{|}{C}}(=O)CH-O-$ | $-SO_2-C_6H_4-CH_3$ |
| 18 | $NC-(CH_2)_3-$ | $-\underset{CH_3}{\underset{|}{C}}(=O)CH-O-\underset{CH_3}{\underset{|}{C}}(=O)CH-O-$ | $-CH_2C(=O)O-Bu(t)$ |

TABLE-continued $$X-O-(CH_2CH_2O)_m-(Y)_n-Z \quad (I)$$

wherein m and n are each optional integer of 2–10,000.

| Compound NO. | X | Y | Z |
|---|---|---|---|
| 19 | NC—(CH$_2$)$_3$— | —CCHOCCHO— with two C=O, CH$_3$, CH$_3$ substituents | (CH$_2$)$_2$CH(OCH$_2$CH$_3$)$_2$ |
| 20 | H$_2$N—(CH$_2$)$_4$— | —CCHOCCHO— with two C=O, CH$_3$, CH$_3$ substituents | SO$_2$—C$_6$H$_4$—CH$_3$ |
| 21 | H$_2$N—(CH$_2$)$_4$— | —CCHOCCHO— with two C=O, CH$_3$, CH$_3$ substituents | CH$_2$CO—Bu(t) with C=O |
| 22 | NC—(CH$_2$)$_3$— | —CCHOCCHO— with two C=O, CH$_3$, CH$_3$ substituents | CH$_2$CH$_2$CHO |
| 23 | NC—(CH$_2$)$_3$— | —CH$_2$C(CH$_3$)(COOCH$_3$)— | H |
| 24 | NC—(CH$_2$)$_3$— | —CH$_2$C(CH$_3$)(COOCH$_3$)— | CH$_2$CH$_2$OH |
| 25 | NC—(CH$_2$)$_3$— | —CH$_2$C(CH$_3$)(COOCH$_3$)— | CH$_2$CH$_2$OCC(CH$_3$)=CH$_2$ with C=O |
| 26 | H$_2$N—(CH$_2$)$_4$— | —CH$_2$C(CH$_3$)(COOCH$_3$)— | H |
| 27 | H$_2$N—(CH$_2$)$_4$— | —CH$_2$C(CH$_3$)(COOCH$_3$)— | CH$_2$CH$_2$OH |
| 28 | H$_2$N—(CH$_2$)$_4$— | —CH$_2$C(CH$_3$)(COOCH$_3$)— | —CH$_2$CH$_2$OCC(CH$_3$)=CH$_2$ with C=O |

TABLE-continued $$X-O-(CH_2CH_2O)_m-(Y)_n-Z \qquad (I)$$

wherein m and n are each optional integer of 2–10,000.

| Compound NO. | X | Y | Z |
|---|---|---|---|
| 29 | NC―(CH₂)₃― | —CH₂C(CH₃)(COOCH₂CH₂OSi(CH₃)₂Bu(t))— | H |
| 30 | H₂N―(CH₂)₄― | —CH₂C(CH₃)(COOCH₂CH₂OH)— | H |
| 31 | Ph―CH=N―CH₂CH₂― | —C(O)CH(CH₃)OC(O)CH(CH₃)O— | C(O)CH=CH₂ |
| 32 | H₂N―(CH₂)₂― | —C(O)CH(CH₃)OC(O)CH(CH₃)O— | C(O)CH=CH₂ |
| 33 | Bu(t)OC(O)―(CH₂)₂― | —C(O)CH(CH₃)OC(O)CH(CH₃)O— | H |
| 34 | Bu(t)OC(O)―(CH₂)₂― | —C(O)CH(CH₃)OC(O)CH(CH₃)O— | C(O)C(CH₃)=CH₂ |
| 35 | HOC(O)―(CH₂)₂― | —C(O)CH(CH₃)OC(O)CH(CH₃)O— | H |
| 36 | HOC(O)―(CH₂)₂― | —C(O)CH(CH₃)OC(O)CH(CH₃)O— | C(O)C(CH₃)=CH₂ |
| 37 | Ph―CH₂S―(CH₂)₂― | —C(O)CH(CH₃)OC(O)CH(CH₃)O— | H |
| 38 | HS―(CH₂)₂― | —C(O)CH(CH₃)OC(O)CH(CH₃)O— | H |

TABLE-continued $$X-O-(CH_2CH_2O)_{\overline{m}}-(Y)_{\overline{n}}Z \quad (I)$$

wherein m and n are each optional integer of 2–10,000.

| Compound NO. | X | Y | Z |
|---|---|---|---|
| 39 | C₆H₅–CH=N–CH₂CH₂– | =CH₂C(CH₃)(COOCH₂CH₂OSi(CH₃)₂Bu(t))– | |
| 40 | H₂N–CH₂CH₂– | –CH₂C(CH₃)(COOCH₂CH₂OH)– | H |

In the above table, Bu(t) denotes —C(CH₃)₃.

The above-mentioned block polymer which is to be provided by this invention can be produced efficiently in accordance with the following reaction schemes.

Reaction from (A) to (II)

Initiator (A) is diluted with an aprotic solvent, and, then, ethylene oxide and hydrophobic monomer (segment Y-derivable monomer) are added in this order to the reaction

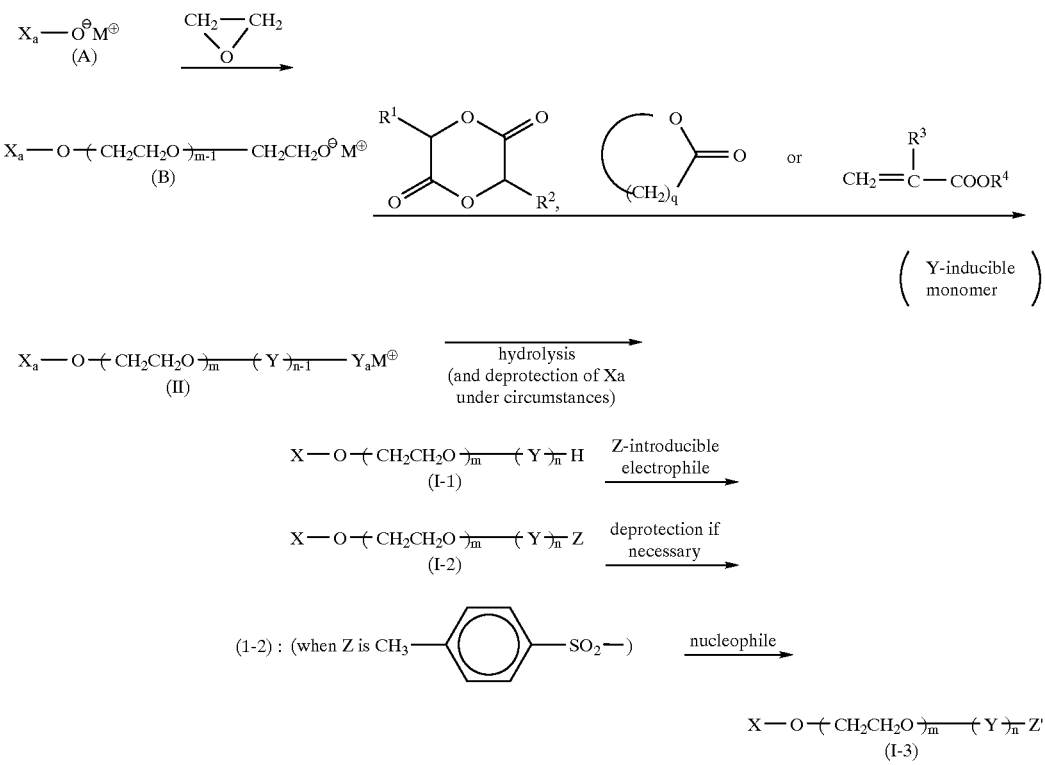

Reaction Scheme (The marks Xa, X, M⊕, Y, Ya and Z in the above reaction are as defined above, and Z' is a residue derived from nucleophile.)

system so that polymerization reaction may proceed. Examples of aprotic solvent include benzene, toluene, hexane, tetrahydrofuran and dioxane. The initiator has a concentration of 0.1 to 95% by weight, preferably 1 to 70% by weight, most preferably 2 to 5% by weight. The ratio of initiator to ethylene oxide is, although polymerization is possible at any ratio according to the desired number of m to be achieved, 1:1 to 1:10,000, preferably 1:1,000, and most preferably 1:200. As for the proportion of initiator to hydrophobic monomer, although any proportion is possible according to the desired number of n to be achieved, it is 1:1 to 1:10,000, preferably 1:1,000, and most preferably 1:200. The reaction is preferably conducted in a pressure glass tube or in an autoclave. Reaction temperature is −50° C.–150° C., preferably 0° C.–100° C., and most preferably 30° C.–50° C. Reaction pressure is 0.1 to 10 kgf/cm² G, preferably 1 to 2 kgf/cm² G. As for reaction time, ethylene oxide is allowed to react normally for 0.01 to 200 hours, preferably 1 to 100 hours, and most preferably 20 to 50 hours, and, after hydrophobic monomer is added to the reaction system, the reaction is continued for further 0.01 to 200 hours, preferably 1 to 100 hours, and most preferably 20 to 50 hours.

Thus obtained living block polymer (II) has a protected functional group at the terminal of initiator (α-terminal) quantitatively and an alkali metal alkoxide at the other terminal (ω-terminal). When the polymer of formula (II) is treated with acid for example, there can be produced a block polymer which has a functional group such as amino group, carboxyl group and mercapto group at α-terminal, and a hydroxyl group at ω-terminal (the case where Y is derived from lactide or lactone). This block polymer is included in the block polymer of formula (I).

Other polymers represented by formula (I) which have various functional groups at ω-terminal are produced by adding electrophile (reactant) to the living block polymer of formula (II) in the above reaction system.

Examples of electrophile include compounds which are represented by the following formula

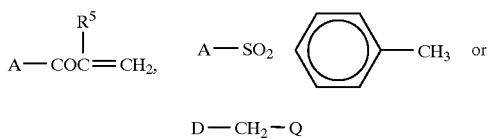

wherein A denotes a group forming an active ester, e.x., a portion forming a halogen atom such as chlorine and bromine or an acid anhydride. D denotes chlorine, bromine or iodine, and Q denotes a functional group-containing group such as

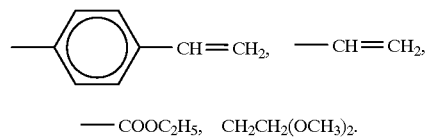

Concrete examples of electrophile include, not restrictively, acrylic acid chloride, acrylic acid anhydride, acrylic acid, methacrylic acid chloride, methacrylic acid anhydride, methacrylic acid, vinylbenzyl chloride, vinylbenzyl bromide, allyl chloride, allyl bromide, allyl iode, p-toluenesulfonic acid chloride, ethyl chloroacetate, ethyl bromoacetate, 2-ethyl chloropropionate and 3,3-dimethoxypropyl bromide.

When Z is p-toluenesulfonyl group and when Y is derived from glycolide or lactone, another functional group can be further introduced by nucleophilic substitution by means of making a nucleophilic reagent react at ω-terminal which has been activated with p-toluenesulfonic acid. These reactions are each conducted by a normal method. Concrete examples of the above nucleophilic reagent include, not restrictively, sodium hydrosulfide, potassium hydrosulfide, sodium 2-aminoethoxide, potassium 2-aminoethoxide and halogen. The protecting group (ester group etc.) at X portion and/or at Z portion of the obtained block polymer of formula (I) may be eliminated, if necessary, by a known hydrolysis reaction, reduction or catalytic hydogenation reaction. In this manner, there can be provided a block polymer of formula (I) wherein functional groups at α-terminal and/or ω-terminal are liberated.

The block polymer of formula (I) includes in its molecule hydrophilic segment and hydrophobic segment. It is possible, therefore, to adjust the balance between hydrophilicity and hydrophobicity by means of selecting species or molecular weight of the segments appropriately. Hence, the block polymer of formula (I) is capable of forming a polymeric micelle in a solvent.

Treatments for preparing polymeric micelle which is composed of the block polymer of formula (I) as a constituent component include heat treatment, ultrasonic treatment and organic solvent treatment which are conducted separately or in combination. As for heat treatment, a mixture of one or more kinds of block polymer of formula (I) is dissolved in water, and the resultant solution is heated to 30–100° C. As for ultrasonic treatment, a mixture of one or more kinds of block polymer of formula (I) is dissolved in water, and the resultant solution is treated in the range from 1 W to 20 W, preferably 2 to 4 W, for one second to 24 hours, preferably 30 minutes to 10 hours, most preferably 2 to 4 hours. As for organic solvent treatment, a mixture of one or more kinds of block polymer of formula (I) is dissolved in an organic solvent, and the resultant solution is dispersed in water, and, thereafter, the organic solvent is evaporated. Examples of organic solvent include methanol, ethanol, tetrahydrofuran, dioxane, chloroform, benzene, toluene, dimethylsulfoxide, dimethylformamide, dimethyl acetamide and methylene chloride. The proportion of water to organic solvent may be optional. However, it is preferably 1 to 1000 times, and preferably by far 5 to 20 times. The treatment is conducted at a temperature ranging from 0 to 100° C., preferably 5 to 25° C. Dialysis can be employed in these methods.

In the following, this invention will be explained in more detail by means of Examples, which do not however restrict the scope of this invention.

EXAMPLE 1

Preparation of a polymer represented by the following formula:

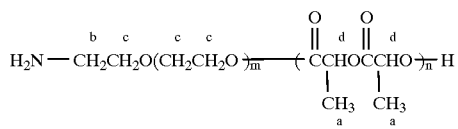

THF 20 ml, 2-benzaliminoethanol 0.15 g and potassium naphthalene 0.5 mol/L-tetrahydrofuran solution 2 ml were added to a reactor and agitated for 3 minutes in an argon atmosphere; a potassium compound of 2-benzaliminoethanol (potassium 2-benzaliminoethoxide) was produced.

Ethyleneoxide 8.8 g was added to this solution and agitated at room temperature under 1 atm. After being reacted for two days, lactide 7.2 g was added to this reaction solution and agitated for another hour. After vacuum removal of the reacted solvent, 1 N-hydrochloric acid 50 ml was added and agitated for 2 hours at room temperature, and the protective group was removed; then this was poured into cold propanol, and the polymer produced was precipitated. The precipitate attained with centrifugal separation was refined by freeze drying from benzene. The yield was 15.0 g (94%). The polymer attained with gel permeation chromatography was mono-modal, and the molecular weight of the polymer was about 15000.

According to proton nuclear magnetic resonance spectra with heavy chloroform of the polymer attained, this polymer was confirmed to be a heterotelechelic oligomer having both units of polyethylene oxide (PEO) and polylactide (PL), and quantitatively having amino group on the α-terminal and hydroxyl group on the ω-terminal. The chain length of the block polymer determined by the integral ratio of the spectra was about 9000 for PEO and about 7000 for PL.

The results of proton nuclear magnetic resonance spectra are as follows:

$^1$H-NMR (DMSO), δ (ppm)

1.6 (a: 294 H)

2.8 (b: 2 H)

3.6 (c: 820 H)

5.2 (d: 98 H)

(The marks a–c correspond to the hydrogen atoms in the above formula. The same applies to the followings.)

EXAMPLE 2

Preparation of a polymer represented by the following formula:

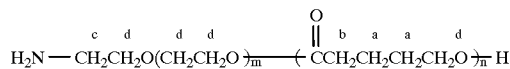

THF 20 ml, 2-benzaliminoethanol 0.15 g, and potassium naphthalene 0.5 mol/L-tetrahydrofuran solution (2 ml) were added to a reactor and agitated for 3 minutes in an argon atmosphere; the potassium compound of 2-benzaliminoethanol (potassium 2-benzaliminoethoxide) was produced.

Ethyleneoxide 8.8 g was added to this solution and agitated at room temperature and at 1 atm. After reaction for 2 days, δ-valerolactone 5.0 g was added to this reaction solution and agitated for another hour. After vacuum removal of the reacted solvent, 1 N-hydrochloric acid 50 ml was added and agitated for 2 hours at room temperature, and the protective group was removed; then this was poured into cold propanol and the polymer produced was precipitated. The precipitate attained with centrifugal separation was refined by freeze drying from benzene. The yield was 12.5 g (90%). The polymer attained with gel permeation chromatography was mono-modal and the molecular weight of the polymer was about 14000.

According to proton nuclear magnetic resonance spectra with chloroform deuteride of the polymer attained, this polymer was confirmed to be a heterotelechelic oligomer having both units of polyethylene oxide (PEO) and poly(δ-valerolactone) (PVL), and quantitatively having amino group on the α-terminal and hydroxy group on the ω-terminal. The chain length of the block polymer determined by the integral ratio of the spectra was about 800 for PEO and about 5200 for PVL.

The results of proton nuclear magnetic resonance spectra are as follows:

$^1$H-NMR (DMSO), δ (ppm)

1.7 (a: 208 H)

2.4 (b: 104 H)

2.8 (c: 2 H)

3.6 (d: 904 H)

EXAMPLE 3

Preparation of a polymer represented by the following formula:

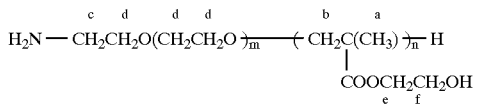

THF 20 ml, 2-benzaliminoethanol 0.15 g and potassium naphthalene 0.5 mol/L-tetrahydrofuran solution (2 ml) were added to a reactor and agitated for 3 minutes in an argon atmosphere; the potassium compound of 2-benzaliminoethanol (potassium 2-benzaliminoethoxide) was produced.

Ethyleneoxide 8.8 g was added to this solution and agitated at room temperature and at 1 atm. After reaction for 2 days, 2-(trimethylsiloxy)ethyl methacrylate 10.0 g was added to this reaction solution and agitated for another hour. After vacuum removal of the reacted solvent, 1 N-hydrochloric acid 50 ml was added and agitated for 2 hours at room temperature, and the protective group was removed; then this was poured into cold propanol and the polymer produced was precipitated. The precipitate attained with centrifugal separation was refined by freeze drying from benzene. The yield was 15.0 (96%). The polymer attained with gel permeation chromatography was mono-modal and the molecular weight of the polymer was about 14000.

According to proton nuclear magnetic resonance spectra with heavy methanol of the polymer attained, this polymer was confirmed to be a heterotelechelic oligomer having both units of polyethylene oxide (PEO) and poly(2-hydroxyethyl methacrylate) (PHEMA), and quantitatively having amino group on the α-terminal. The chain length of the block polymer determined by the integral ratio of the spectra was about 8800 for PEO and about 7000 for PHEMA.

The results of proton nuclear magentic resonance spectra are as follows:

$^1$H-NMR (DMSO), δ (ppm)

0.9–1.3 (a: 150 H)

2.0 (b: 100 H)

2.8 (c: 2 H)

3.6 (d: 800 H)

3.8 (e: 100 H)

4.1 (f: 100 H)

EXAMPLE 4

Preparation of a polymer represented by the following formula:

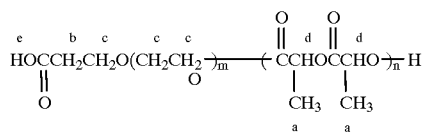

THF 20 ml, tert-butoxycarbonylethanol 0.13 g and potassium naphthalene 0.5 mol/L-tetrahydrofuran solution 2 ml were added to a reactor and agitated for 3 minutes in an argon atmosphere; the potassium compound of tert-butoxycarbonylethanol (potassium tert-butoxycarbonylethoxide) was produced.

Ethyleneoxide 8.8 g was added to this solution and agitated at room temperature and at 1 atm. After reaction for 2 days, lactide 7.2 g was added to this reaction solution and agitated for another hour. After vacuum removal of the reacted solvent, 1 N-hydrochloric acid 50 ml was added and agitated for 2 hours at room temperature, and protective group was removed; then this was poured into cold propanol and the polymer produced was precipitated. The precipitate attained with centrifugal separation was refined by freeze drying from benzene. The yield was 14.0 g (88%). The polymer attained with gel permeation chromatography was mono-modal and the molecular weight of the polymer was about 14000.

According to proton nuclear magnetic resonance spectra with heavy chloroform of the polymer attained, this polymer was confirmed to be a heterotelechelic oligomer having both units of polyethylene oxide (PEO) and polylactide (PL), and quantitatively having carboxyl group on the α-terminal and hydroxyl group on the ω-terminal. The chain length of the block polymer determined by the integral ratio of the spectra was about 8000 for PEO and about 6000 for PL.

The results of proton nuclear magnetic resonance spectra are as follows:
$^1$H-NMR (DMSO), δ (ppm)
1.6 (a: 252 H)
2.4 (b: 2 H)
3.6 (c: 730 H)
5.2 (d: 84 H)
9.8 (e: 1 H)

EXAMPLE 5

Preparation of a polymer represented by the following formula:

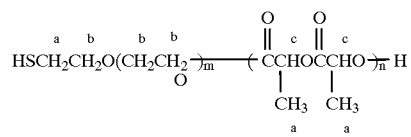

THF 20 ml, benzylthiol 0.13 g and potassium naphthalene 0.5 mol/L-tetrahydrofuran solution 2 ml were added to a reactor and agitated for 3 minutes in an argon atmosphere; the potassium compound of benzylthiol (benzylthiopotassium) was produced.

Ethyleneoxide 8.8 g was added to this solution and agitated at room temperature and at 1 atm. After reaction for 2 days, lactide 7.2 g was added to this reaction solution and agitated for another hour. After vacuum removal of the reacted solvent, aqueous solution of sodium boron hydride 50 ml was added and agitated for 2 hours at room temperature, and the protective group was removed; then this was poured into cold propanol and the polymer produced was precipitated. The precipitate attained with centrifugal separation was refined by freeze drying from benzene. The yield was 14.5 g (91%). The polymer attained with gel permeation chromatography was mono-modal and the molecular weight of the polymer was about 16000.

According to proton nuclear magentic resonance spectra with heavy chloroform of the polymer attained, this polymer was confirmed to be a heterotelechelic oligomer having both units of polyethylene oxide (PEO) and polylactide (PL), and quantitatively having mercapto group on the α-terminal and hydroxyl group on the ω-terminal.

The results of proton nuclear magnetic resonance spectra are as follows:
$^1$H-NMR (DMSO), δ (ppm)
1.6 (a: 300 H)
3.6 (b: 800 H)
5.2 (c: 100 H)

EXAMPLE 6

Preparation of a polymer represented by the following formula:

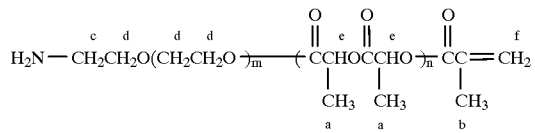

THF 20 ml, 2-benzaliminoethanol 0.15 g and potassium naphthalene 0.5 mol/L-tetrahydrofuran solution 2 ml were added to a reactor and agitated for 3 minutes in an argon atmosphere; a potassium compound of 2-benzaliminoethanol (potassium 2-benzaliminoethoxide) was produced.

Ethyleneoxide 8.8 g was added to this solution and agitated at room temperature and at 1 atm. After reaction for 2 days, lactide 7.2 g was added to this reaction solution and agitated for another hour. After vacuum removal of the reacted solvent, 0.1 N-hydrochloric acid 50 ml was added and agitated for 2 hours at room temperature, and the protective group was removed; then this was poured into cold propanol and the polymer produced was precipitated. The precipitate attained with centrifugal separation was refined by freeze drying from benzene. The yield was 14.0 g (88%). The polymer attained with gel permeation chromatography was mono-modal and the molecular weight of the polymer was about 15000.

According to proton nuclear magnetic resonance spectra with heavy chloroform of the polymer attained, this polymer was confirmed to be a heterotelechelic oligomer having both units of polyethylene oxide (PEO) and polylactide (PL), and quantitatively having amino group on the α-terminal and methacryloyl group on the ω-terminal. The chain length of the block polymer determined by the integral ratio of the spectral was about 8800 for PEO and about 6800 for PL.

The results of proton nuclear magnetic resonance spectra are as follows:

$^1$H-NMR (DMSO), δ (ppm)

1.6 (a: 283 H)

1.9 (b: 3 H)

2.8 (c: 2 H)

3.6 (d: 800 H)

5.2 (e: 94 H)

5.7, 6.2 (f: 2H)

EXAMPLE 7

Preparation of a polymer represented by the following formula:

$$\text{NC}\overset{a}{-}\overset{b}{\text{CH}_2}\overset{c}{\text{CH}_2\text{CH}_2\text{O}}\overset{c}{-}(\overset{c}{\text{CH}_2\text{CH}_2\text{O}})_m-(\overset{O}{\overset{\|}{\text{C}}}\text{CHO}\overset{O}{\overset{\|}{\text{C}}}\text{CHO})_n\text{H}$$
$$\underset{e}{\text{CH}_3}\ \underset{e}{\text{CH}_3}$$

A reactor was charged with 20 ml of THF, 0.04 g of acetonitrile and 2 ml of solution of potassium naphthalene dissolved in tetrahydrofuran in a concentration of 0.5 mol/L-tetrahydrofuran, and the resulting mixture was stirred for three minutes in an argon atmosphere, and, thus, there was formed cyanomethyl potassium.

There was added 4.4 g of ethylene oxide to the resulting solution, which was then stirred at 1 atm and at a room temperature. After two days-reaction was over, 7.2 g of lactide was added to the reaction liquid, which was then allowed to react for further one hour. Thus produced solution was poured into cooled propanol, after the reaction solvent had been distilled off, so that the formed polymer might be precipitated. Centrifugalized precipitate was purified by freeze drying from benzene. The yield was 11.0 g (95%). Gel permeation chromatography taught that the polymer obtained was mono-modal and had a number average molecular weight of about 11,000.

Results of proton nuclear magnetic resonance spectra were as follows:

$^1$H-NMR (CDCl$_3$), δ (ppm)

2.4 (a: 2 H)

1.8 (b: 2 H)

3.6 (c: 400 H)

5.2 (d: 50 H)

1.6 (e: 150 H)

EXAMPLE 8

Preparation of a polymer represented by the following formula:

$$\text{NC}\overset{a}{-}\overset{b}{\text{CH}_2}\overset{c}{\text{CH}_2\text{CH}_2\text{O}}(\overset{d}{\text{CH}_2}\overset{d}{\text{CH}_2\text{O}})_m-(\overset{O}{\overset{\|}{\text{C}}}\overset{e}{\text{CHO}}\overset{O}{\overset{\|}{\text{C}}}\overset{e}{\text{CHO}})_n-\overset{O}{\overset{\|}{\text{C}}}\overset{g}{\text{C}}=\text{CH}_2$$
$$\underset{f}{\text{CH}_3}\ \underset{f}{\text{CH}_3}\ \underset{h}{\text{CH}_3}$$

A reactor was charged with 20 ml of THF, 0.04 g of acetonitrile and 2 ml of solution of potassium aphthalene dissolved in tetrahydrofuran in a concentration of 0.5 mol/L-tetrahydrofuran, and the resulting ixture was stirred for three minutes in an argon atmosphere, and, thus, there was formed cyanomethyl potassium.

There was added 4.4 g of ethylene oxide to the resulting solution, which was then stirred at 1 atm and at a room temperature. After two days-reaction was over, 7.2 g of lactide was added to the reaction liquid, which was then allowed to react for further one hour.

Next, there was added 10 g of methacrylic acid anhydride to this system, which was then allowed to react for further two hours at a room temperature. Thus produced solution was poured into cooled propanol, after the reaction solvent had been distilled off, so that the formed polymer might be precipitated. Centrifugalized precipitate was purified by freeze drying from benzene. The yield was 10.5 g (91%). Gel permeation chromatography taught that the polymer obtained was mono-modal and had a number average molecular weight of about 11,000.

Results of proton and carbon nuclear magnetic resonance spectra were as follows:

$^1$H-NMR (CDC$_3$), δ (ppm)

1.6 (f: 150 H)

1.8 (b: 2 H)

1.9 (h: 3 H)

2.4 (a: 2 H)

3.6 (c, d: 400 H)

5.2 (e: 50H)

5.6 6.2 (g: 2H)

$^{13}$C-NMR (CDCl$_3$), δ (ppm)

13.9 (2)*

16.5 (10)

18.0 (8)

25.2 (3)

64.2 (7)

69.2 (9)

68.8 (4)

70.0 (5, 6)

119.4 (1)

126.5 (13)

135.2 (12)

169.5 (8, 11)

* The figures in parentheses each correspond to the carbon atom in the following formula

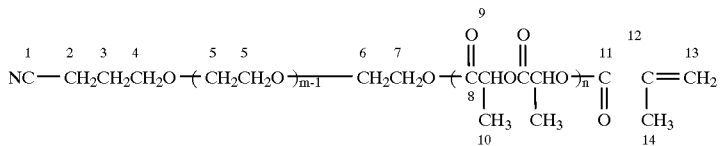

EXAMPLE 9

Preparation of a polymer represented by the following formula:

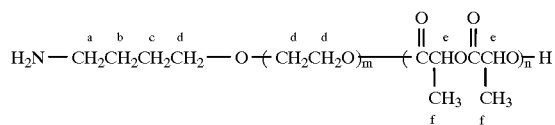

There was dissolved 200 mg of the polymer obtained in Example 7 into 40 ml of ammonia-saturated methanol, and the resulting solution was hydrogenated at 25° C. and 35 atm with use of 0.5 g of Raney-Ni-W2. One hour after, the reaction solvent was distilled off, and, thus, polymer was recovered with cooled propanol. The yeild of the polymer obtained by freeze drying from benzene was 180 mg (90%). Gel permeation chromatography taught that the polymer obtained was mono-modal and had a number average molecular weight of about 11,000.

Results of proton and carbon nuclear magnetic resonance spectra were as follows:

$^1$H-NMR (CDCl$_3$), δ (ppm)

1.6 (b, f: 150 H)
1.8 (c: 2 H)
2.7 (a: 2 H)
3.6 (d: 400 H)
5.2 (e: 50H)

$^{13}$C-NMR (CDC$_3$), δ (ppm)

16.5 (10)*
25.1 (3)
26.4 (2)
40.9 (1)
64.2 (7)
68.8 (4)
69.2 (9)
70.0 (5, 6)
169.4 (8)

* The figures in parentheses each correspond to the carbon atom in the following formula:

EXAMPLE 10

Preparation of polymeric micelle

The block copolymer sample 50 mg obtained in Example 1 was dissolved in water or an appropriate buffered solution so that concentration might become 0.01 to 0.1% (w/v). With particle distribution measurement by dynamic light scattering, the formation of a single polymer micelle with average grain diameter of 30 nm was confirmed in the solution. The critical micelle concentration of this polymer micelle was 10 mg/L. From the results of structural analysis, this polymer micelle was found to be a new polymer micelle having an amino group on the micelle surface.

EXAMPLE 11

Preparation of polymeric micelle

The block copolymer sample 50 mg obtained in Example 4 was dissolved in water or an appropriate buffered solution so that concentration might become 0.01 to 0.1% (w/v). With particle distribution measurement by dynamic light scattering, the formation of a single polymer micelle with average grain diameter of 28 nm was confirmed in the solution. The critical micelle concentration of this polymer micelle was 11 mg/L. From the results of structural analysis, this polymer micelle was found to be a new polymer micelle having a carboxyl group on the micelle surface.

EXAMPLE 12

Preparation of polymeric micelle

The block copolymer sample 50 mg obtained in Example 6 was dissolved in water so that concentration might become 0.1% (w/v). With particle distribution measurement by dynamic light scattering, the formation of a single polymer micelle with average grain diameter 30 nm was confirmed in the solution. The critical micelle concentration of this polymer micelle was 10 mg/L. Benzoyl peroxide 0.01 g was solubilized in this micelle solution and reacted for 5 hours at 80° C. After the reaction, it underwent dialysis against water with a fractional molecular weight 12000 membrane filter, and from the results of structural analysis, this polymer micelle was found to have the average grain diameter 30 nm, unchanged from before the reaction. The micelle diameter

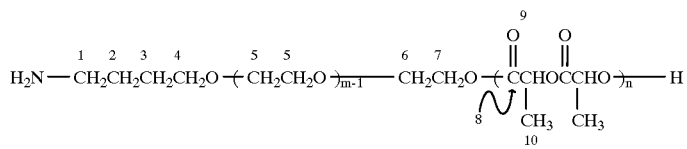

was not changed even by the addition of dodecyl sulfate, and it was confirmed that the micelles were effectively crosslinked. From the results of structural analysis, this polymer micelle was found to be a new crosslinked polymer micelle having an amino group on the micelle surface.

INDUSTRIAL APPLICABILITY

This invention provides a block polymer which has at its both ends functional groups such as amino group, carboxyl group, hydroxyl group and mercapto group which a protein usually has, and which, under circumstances, has a vinyl group which may further be polymerized. Moreover, the balance between hydrophilicity and hydrophobicity in the molecule can be adjusted adequately. This block polymer can therefore be advantageously used in the field of production and processing of bio-compatible materials.

Furthermore, it is possible to efficiently bind molecules of living organism such as antibody to the polymeric micelle compounds which are produced from the above polymer and which have on their surface functional groups such as amino group, carboxyl group and mercapto group, since said micelle has the following characteristics:

1) Drugs can be introduced into the nucleus of micelle;

2) Owing to ω-terminal functional group, there can be prepared a stable crosslinked micelle (nanosphere); and 3) Surface functional groups are stable in water and are capable of reacting with amine or thiol.

On the other hand, polyethylene oxide chain, poly-glycol acid and polylactone, which are segments constituting the block polymer of this invention, are each known to be decomposed in a living organism, and, therefore, electric charge on the surface of polymeric micelle can be freely changed. Fom these facts, we can expect that the polymeric micelle compounds which are provided by this invention and which have on their surface functional groups will be applicable as i) carrier for drug delivery to a certain organ and ii) medicine such as diagnostic nanosphere.

Hence, there is a possibility that this invention will be applied in the field of medical treatment.

We claim:

1. A block polymer which is represented by formula (I) below:

wherein X denotes an alkyl group having 1 to 10 carbon atoms which has one or two substituents selected from the group consisting of amino group blocked with amino-protecting group, carboxyl group blocked with carboxyl-protecting group and mercapto group blocked with mercapto-protecting group, or phenyl or phenylalkyl group which has the above-mentioned substituents on benzene ring;

Y denotes a group selected from the group consisting of the following recurring units

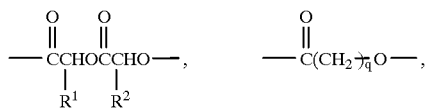

-continued

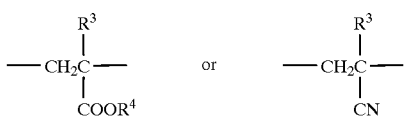

wherein $R^1$ and $R^2$ independently denote hydrogen atom or alkyl group having 1 to 5 carbon atoms; $R^3$ denotes hydrogen atom or methyl group; $R^4$ denotes alkyl group having 1 to 5 carbon atoms which is substituted with hydroxyl group under circumstances; q denotes an integer of 2–5;

Z denotes functional group selected from the group consisting of hydrogen atom, acryloyl group ($CH_2$=CH—CO—), methacryloyl group ($CH_2$=C($CH_3$)—CO—),

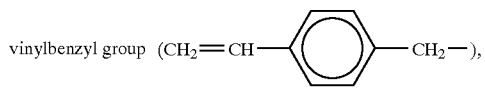

allyl group ($CH_2$=CH—$CH_2$—),

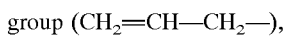

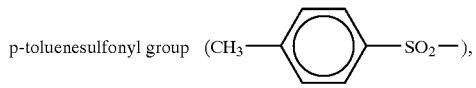

mercapto group, alkyl group having amino group which is mono- or di-substituted under circumstances with alkyl group having 1 to 5 carbon atoms, alkyl group having carboxyl group or its ester group, alkyl group having aldehyde or its acetal group, and halogen atom; and m and n independently denote an integer of 2–10,000.

2. The block polymer of claim 1 wherein X denotes an alkyl group having 1 to 10 carbon atoms which is substituted with amino group, carboxyl group or mercapto group which is not blocked with protecting group.

3. The block polymer of claim 1 wherein X denotes an alkyl group having 1 to 10 carbon atoms which is substituted with amino group blocked with amino-protecting group selected from the group consisting of alkoxycarbonyl group having 1 to 5 carbon atoms; benzylidene group whose benzene ring is substituted under circumstances with alkyl group having 1 to 3 carbon atoms or with halogen atom; silyl group having three groups selected from the group consisting of alkyl group having 1 to 3 carbon atoms and phenyl group; and cyano group, or carboxyl group blocked with carboxy-protecting group selected from the group consisting of alkoxy group having 1 to 5 carbon atoms; benzyloxy group; diphenylmethoxy group; triphenylmethoxy group; and cyano group, or mercapto group blocked with mercapto-protecting group selected from the group consisting of phenyl and benzyl.

4. The block polymer of claim 1 wherein X denotes an alkyl group having 1 to 10 carbon atoms which is substituted with amino group blocked with amino-protecting group which is benzylidene group, trimethylsilyl group or cyano group, or substituted with carboxyl group blocked with carboxy-protecting group which is tert.-butoxy group.

5. The block polymer of claim 1 wherein X denotes an alkyl group having 1 to 10 carbon atoms which is substituted with amino group or carboxyl group which is not blocked with protecting group.

6. The block polymer of claim 1 wherein Y denotes recurring units represented by the following formulae

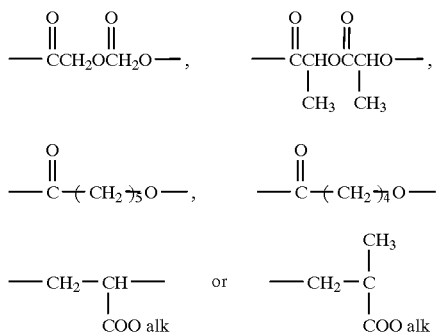

wherein alk denotes an alkyl group having 1 to 3 carbon atoms which is substituted, under circumstances, with hydroxyl group.

7. The block polymer of claim 1 wherein Z denotes hydrogen atom, acryloyl group or methacryloyl group.

8. A living block polymer represented by the following formula (II):

wherein Xa denotes an alkyl group having 1 to 10 carbon atoms which has one or two substituents selected from the group consisting of amino group blocked with amino-protecting group, carboxyl group blocked with carboxyl-protecting group and mercapto group blocked with mercapto-protecting group, or denotes a phenyl or phenyl-alkyl group which has the above-mentioned substituents on benzene ring;

Y and Ya each denote a group selected from the group consisting of groups represented by the following formulae

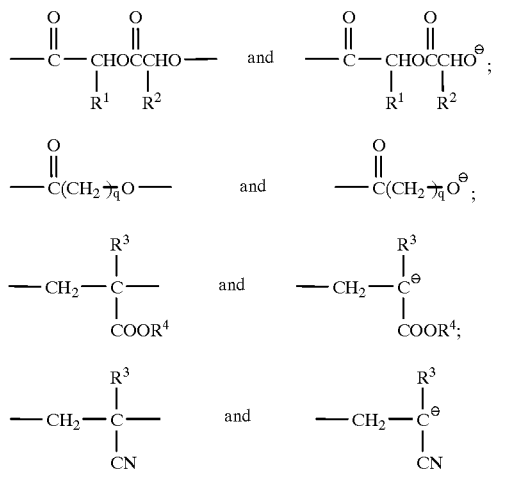

wherein $R^1$ and $R^2$ independently denote hydrogen atom or alkyl group having 1 to 5 carbon atoms; $R^3$ denotes hydrogen atom or methyl group; $R^4$ denotes alkyl group having 1 to 5 carbon atoms which is substituted with hydroxyl group under circumstances; and q denotes an integer of 2–5;

$M^{\oplus}$ denotes cation of alkaline metal selected from the group consisting of lithium, sodium, potassium and cesium; and m and n independently denote an integer of 2–10,000.

9. A method to produce the block polymer of claim 1 which comprises the following steps:

(1) a step wherein the living block polymer represented by the following formula (II):

wherein Xa denotes an alkyl group having 1 to 10 carbon atoms which has one or two substituents selected from the group consisting of amino group blocked with amino-protecting group, carboxyl group blocked with carboxyl-protecting group and mercapto group blocked with mercapto-protecting group, or denotes a phenyl or phenyl-alkyl group which has the above-mentioned substituents on benzene ring;

Y and Ya each denote a group selected from the group consisting of groups represented by the following formulae

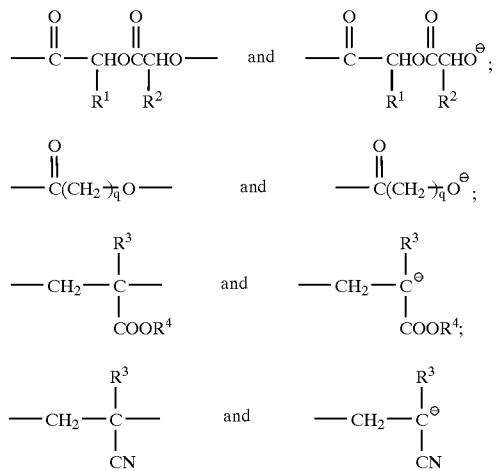

wherein $R^1$ and $R^2$ independently denote hydrogen atom or alkyl group having 1 to 5 carbon atoms; $R^3$ denotes hydrogen atom or methyl group; $R^4$ denotes alkyl group having 1 to 5 carbon atoms which is substituted with hydroxyl group under circumstances; and q denotes an integer of 2–5;

$M^{\oplus}$ denotes cation of alkaline metal selected from the group consisting of lithium, sodium, potassium and cesium; and m and n independently denote an integer of 2–10,000.

is made to react in an inert solvent with an electrophile which is represented by the following formula

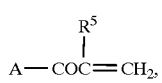

wherein A denotes a group forming an active ester, D denotes chlorine, bromine or iodine, and Q denotes

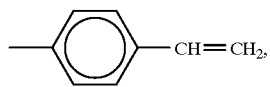

—CH=CH$_2$, —COOC$_2$H$_5$ or —CH$_2$CH$_2$(OCH$_3$)$_2$, (2) a step to convert, if necessary,

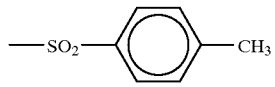

bound to Ya into mercapto group, amino group which is mono- or di-substituted under circumstances with an alkyl group having 1 to 5 carbon atoms, carboxyl group or halogen atom, with use of a corresponding nucleophilic reagent, and (3) a step to eliminate, if necessary, the protecting group of Xa.

10. A polymeric micelle which comprises the block polymer of claim 1 as an effective ingredient.

* * * * *